United States Patent
Kim et al.

(10) Patent No.: US 8,370,290 B2
(45) Date of Patent: Feb. 5, 2013

(54) MUSIC SELECTING SYSTEM AND METHOD THEREOF

(75) Inventors: Yoon Sang Kim, Gyeonggi-do (KR); Goon-Ho Choi, Daejeon (KR)

(73) Assignees: Hyundai Motor Company, Seoul (KR); Korea University of Technology and Education Industry-University Cooperation Foundation, Cheonan, Chungcheongnam-Do (KR)

( * ) Notice: Subject to any disclaimer, the term of this patent is extended or adjusted under 35 U.S.C. 154(b) by 649 days.

(21) Appl. No.: 12/573,290

(22) Filed: Oct. 5, 2009

(65) Prior Publication Data

US 2010/0145203 A1    Jun. 10, 2010

(30) Foreign Application Priority Data

Dec. 4, 2008  (KR) ................. 10-2008-0122648

(51) Int. Cl.
 *G06F 15/00* (2006.01)
 *G06F 15/18* (2006.01)
(52) U.S. Cl. ......................................... 706/62
(58) Field of Classification Search .............. 706/62
 See application file for complete search history.

(56) References Cited

U.S. PATENT DOCUMENTS

| 7,514,623 B1* | 4/2009 | Spinler et al. ................ 84/612 |
| 2007/0113726 A1* | 5/2007 | Oliver et al. ................ 84/615 |
| 2008/0188354 A1* | 8/2008 | Pauws et al. ................ 482/8 |
| 2011/0040707 A1* | 2/2011 | Theisen et al. ................ 706/12 |

FOREIGN PATENT DOCUMENTS

| JP | 2004-090724 A | 3/2004 |
| JP | 2004-254750 A | 9/2004 |
| JP | 2005-095408 A | 4/2005 |
| KR | 1999-0009134 A | 2/1999 |
| KR | 10-2003-0092952 A | 12/2003 |
| KR | 10-2006-0070266 A | 6/2006 |
| KR | 2006-0069807 A | 6/2006 |
| KR | 10-2008-0054252 A | 6/2008 |
| KR | 2002-0046662 A | 9/2010 |

* cited by examiner

*Primary Examiner* — Kakali Chaki
*Assistant Examiner* — Vincent Gonzales
(74) *Attorney, Agent, or Firm* — Edwards Wildman Palmer LLP; Peter F. Corless

(57) ABSTRACT

The present invention relates to a music selecting system and method, and more particularly, to a technology that suitably determines an emotional quotient of user by preferably using a heart rate and biorhythm of user, and automatically selecting music of specific genre according to the determined emotional quotient, a current time and an age.

20 Claims, 14 Drawing Sheets

| heart rate / biorhythm | fast (+11) | middle (-10 ~ 10) | slow (-9) |
|---|---|---|---|
| high(4 ~ 100) | 70 | 60 | 50 |
| middle(-34 ~ 33) | 60 | 50 | 40 |
| low(-100 ~ -33) | 50 | 40 | 30 |

Fig.9

| | |
|---|---|
| early morning (00:00 ~ 06:00) | 0 |
| office-going hour (06:00 ~ 09:00) | 20 |
| forenoon (09:00 ~ 12:00) | -10 |
| lunchtime (12:00 ~ 14:00) | 10 |
| afternoon (14:00 ~ 18:00) | 0 |
| evening (18:00 ~ 24:00) | -10 |

Fig.10

| | |
|---|---|
| one's twenties | 5% |
| one's thirties | 30% |
| one's forties | 40% |
| one's fifties | 50% |
| one's sixties | 55% |
| one's seventies | 60% |

MUSIC SELECTING SYSTEM AND METHOD THEREOF

CROSS-REFERENCE TO RELATED APPLICATION

This application claims under 35 U.S.C. §119(a) the benefit of Korean Patent Application No. 10-2008-0122648 filed Dec. 4, 2008, the entire contents of which are incorporated herein by reference.

BACKGROUND OF THE INVENTION

The present invention relates to a music selecting system and a method that performs a selection of music suitable for a psychological state of a user by inferring the psychological state of the user through a heart rate measurement.

In general, apparatuses which are capable of automatically performing the selection of music that is based on the various psychological states of a user have been suggested. However, such suggested systems have not been able to be put to practical use since a suitable technique to measure the psychological state has not been described.

Accordingly, if a suitable emotional quotient of the user is determined by using the heart rate and biorhythm of the user, and a suitably specific genre of music can be automatically selected according to the determined emotional quotient, a time and an age, then, a music that suitably corresponds to the mood of the user can preferably be selected.

Accordingly, there remains a need in the art for the development of such an automatic music selection apparatus.

The above information disclosed in this the Background section is only for enhancement of understanding of the background of the invention and therefore it may contain information that does not form the prior art that is already known in this country to a person of ordinary skill in the art.

SUMMARY OF THE INVENTION

The present invention provides a music selecting system and method that that suitably determines an emotional quotient of a user by preferably using a heart rate and biorhythm of the user and then automatically selects music of specific genre according to the suitably determined emotional quotient, a current time and an age.

Preferably, a music selecting system according to an exemplary embodiment of the present invention includes, but is not limited to, a heart rate measurement unit that measures a heart rate of the user; a biorhythm calculation unit that calculates a biorhythm index of the user; a music database that stores at least one music file for each of a plurality genres; and a controller that calculates an emotional quotient by using the heart rate and biorhythm index of the user, and then suitably selects a music file of a specific music genre for the user in consideration of a suitable genre combination quotient, preferably according to the emotional quotient, a current time quotient and an age. In accordance with another preferred embodiment of the present invention, the controller suitably calculates a music genre reflection rate according to the user by preferably using the genre combination quotient and then suitably selects the music file according to the calculated music genre reflection rate. In accordance with another preferred embodiment of the present invention, a music selecting system preferably further includes an emotional quotient database that suitably stores emotional quotients according to a biorhythm index by heartbeat quotient according to a difference between an average heart rate of the user which is previously registered and a current heart rate of the user; a time quotient database that suitably stores a time quotient by time; and a genre combination quotient database that suitably stores a genre combination quotient by emotional quotient and time and a genre combination quotient by age. In accordance with another preferred embodiment of the present invention, the heart rate measurement unit preferably includes, but is not limited to, a sound collecting unit that collects a sound generated in a body of the user; an inside microphone that preferably converts the collected sound into an electrical signal; an outer microphone that suitably measures a noise generated in the inside of vehicle; an external noise filter that suitably filters a sound which is similar to a noise of the inside of vehicle measured in the outer microphone in a sound which is converted into an electrical signal in the inside microphone; an external noise filter that suitably filters a sound which is similar to the measured sound from the converted sound; an internal noise filter that preferably filters a noise of preset band from the sound filtered in the external noise filter; and a calculation unit that suitably analyzes time intervals between values of the amplified sound and then suitably calculates a heart rate per hour by using a time interval which most frequently happens among the time intervals. In accordance with another preferred embodiment of the present invention, the sound collecting unit and the inside microphone are suitably comprised of an independent device including a wireless communications module to suitably send the sound which is converted into an electrical signal through the wireless communications module to the external noise filter. In accordance with further preferred embodiments of the present invention, the calculation unit squares all values which are suitably larger or smaller than a mean value among the sound values, extracts sound values which are higher than a given value among the squared sound values and calculates time intervals between the extracted sound values, and calculates a heart rate per hour by using a time interval which most frequently happens among the time intervals. Preferably, in accordance with another preferred embodiment of the present invention, the music database stores at least one music file for each of music genres including, but not limited to, for example, a classical, a ballad and a dance. In accordance with another preferred embodiment of the present invention, a music selecting system preferably further includes a playing unit that plays a music file that is suitably selected by the controller through a speaker; and a key input unit that preferably receives an age from a user. In accordance with further preferred embodiments of the present invention, a music selecting system further includes a user satisfaction level confirmation unit that suitably receives a satisfaction level of music file selected through the key input unit and then sends it to the controller, and then further suitably modifies a genre combination quotient stored in a suitable genre combination quotient database through the satisfaction level of the sent music file.

A music selecting method according to another aspect of the present invention includes: (a) measuring a heart rate of a user; (b) calculating a biorhythm index of the user; and (c) calculating an emotional quotient by using the heart rate and biorhythm index of the user, and selecting a music file of a specific music genre for the user in consideration of a genre combination quotient according to the emotional quotient, a current time quotient and an age.

In accordance with exemplary embodiments of the present invention, in the step of (c), a music genre reflection rate according to user is suitably calculated by using the genre combination quotient and the music files are suitably selected according to the calculated music genre reflection rate. In accordance with further preferred embodiments of the present invention, the step of (a) includes: (a-1) suitably collecting a sound generated in a body of the user; (a-2) converting the collected sound into a suitable electrical signal; (a-3) measuring a noise generated in the inside of vehicle; (a-4) filtering a sound which is suitably similar to a noise of the inside of vehicle measured in an outer microphone in a sound which is converted into an electrical signal in an inside microphone; (a-5) suitably filtering a noise of preset band in an external noise filter; (a-6) suitably amplifying a sound filtered in an internal noise filter; and (a-7) suitably calculating a heart rate per hour by using a time interval which most frequently happens among the time intervals by analyzing time intervals between values of the amplified sound. In accordance with certain exemplary embodiments of the present invention, the step of (a-7) squares all values which are suitably larger or smaller than a mean value among the amplified sound values, extracts sound values which are higher than a given value among the squared sound values and then suitably calculates time intervals between the extracted sound values, and suitably calculates a heart rate per hour by using a time interval which most frequently happens among the time intervals.

According to preferred embodiments of the present invention as described herein, the music selecting system and method of the invention suitably calculates an emotional quotient by using the heart rate and biorhythm index of the user, and then suitably selects a music file in consideration of a genre combination according to the emotional quotient, a current time and an age. Accordingly, the music file according to the preferred music genre corresponding to the psychological state of the user can be played, and in further exemplary embodiments, a high satisfaction rate is achieved, wherein a satisfaction rate corresponding to "very satisfied" of more than 60% is achieved and a satisfaction rate corresponding to "satisfied" of more than 40% is achieved. In further embodiments, the music selecting system of the invention suitably measures a heart rate, preferably an exact heart rate, by measuring the heart rate of the user through a time-interval analysis between sound values which have a similar magnitude in the value of a sound measured in a body of the user.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum).

As referred to herein, a hybrid vehicle is a vehicle that has two or more sources of power, for example both gasoline-powered and electric-powered.

The above features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF THE DRAWINGS

The above and other features of the present invention will now be described in detail with reference to certain exemplary embodiments thereof illustrated by the accompanying drawings which are given hereinafter by way of illustration only, and thus are not limitative of the present invention, and wherein:

FIG. 9 is a configuration diagram showing a configuration of an exemplary emotional quotient database of a music selecting system of the present invention.

FIG. 10 is a configuration diagram showing a configuration of an exemplary time quotient database of music selecting system of the present invention.

FIGS. 12a and 12b show a configuration of genre combination quotient by age of an exemplary music selecting system of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

In a first aspect, the present invention features a music selecting system, comprising a heart rate measurement unit that measures a heart rate of a user a biorhythm calculation unit that calculates a biorhythm index of the user a music database that stores at least one music file, and a controller that selects a music file.

In one embodiment, the music database stores at least one music file for one or more music genres.

In another embodiment, the controller calculates an emotional quotient by using the heart rate and biorhythm index of the user.

In a further embodiment, the controller further selects a music file of a specific music genre for the user in consideration of a genre combination quotient according to the emotional quotient, a current time quotient and an age.

The invention also features a motor vehicle comprising the music selecting system of any one of the aspects described herein.

In another aspect, the invention features a music selecting method, comprising measuring a heart rate of a user, calculating a biorhythm index of the user; and calculating an emotional quotient by using the heart rate and biorhythm index of the user, and selecting a music file for the user.

In one embodiment, the music file is of a specific music genre.

In another embodiment, the selection of a music file for the user is in consideration of a genre combination quotient according to the emotional quotient, a current time quotient and an age.

Hereinafter, exemplary embodiments of the present invention will be described in detail with reference to the attached drawings.

Figure 1:
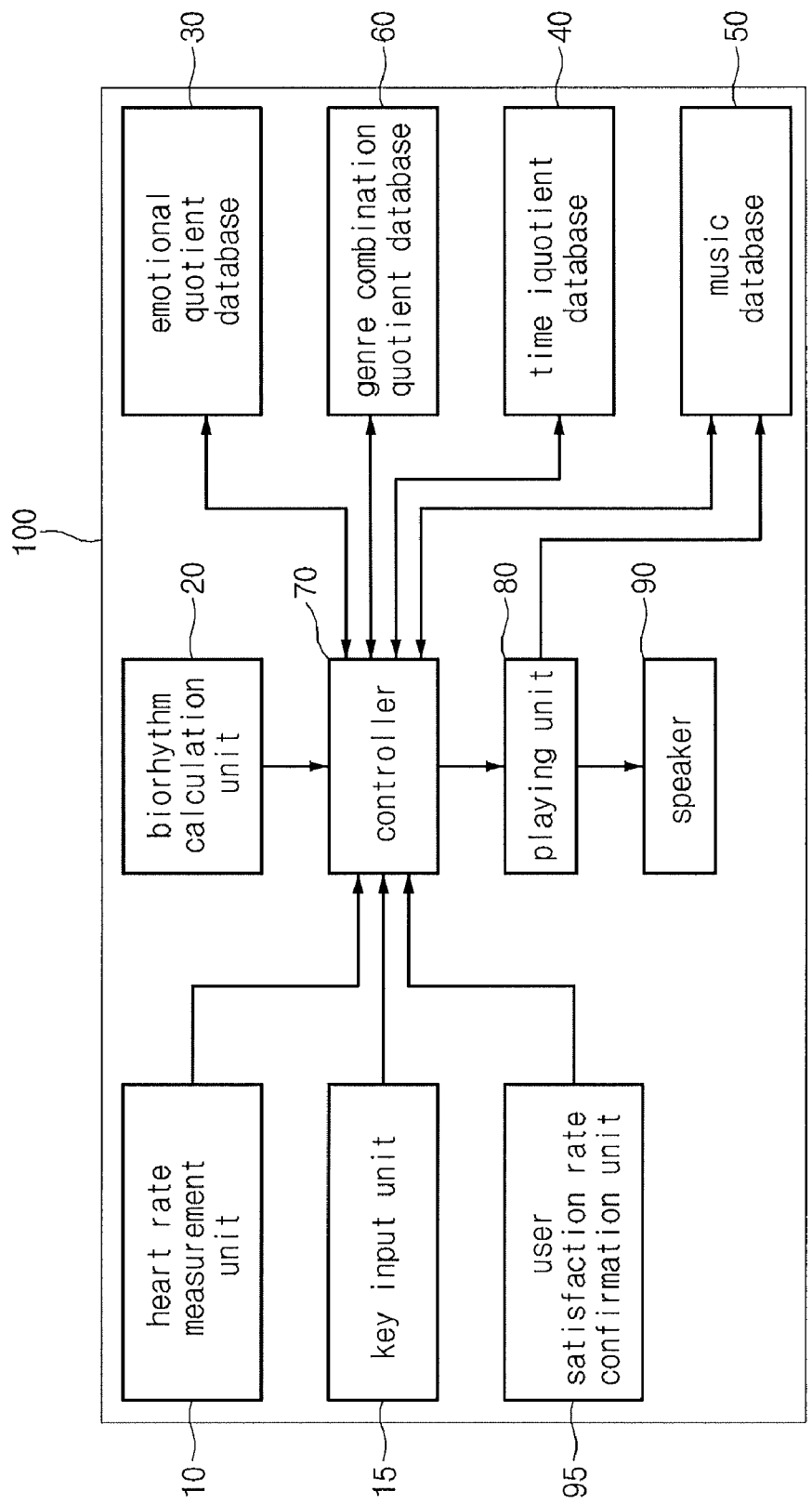
FIG. 1 is a block diagram showing a configuration of an exemplary music selecting system of the present invention.

In one exemplary embodiment of the present invention, for example as shown in FIG. 1, a block diagram shows a preferred configuration of a music selecting system 100 of the present invention.

Preferably, as shown in FIG. 1, firstly, the music selecting system 100 of the present invention includes, but may not be limited only to, a heart rate measurement unit 10, a key input unit 15, a biorhythm calculation unit 20, an emotional quotient database 30, a time quotient database 40, a music database 50, a genre combination quotient database 60, a controller 70, a playing unit 80, a speaker 90, and a user satisfaction level confirmation unit 95.

Preferably, the heart rate measurement unit 10 is installed in a part which is suitably contactable to the body of the user, for example, but not only limited to, in a safety belt or steering wheel of vehicle, and measures the heart rate of the user. The heart rate measurement unit 10 is installed in any part which is suitably contactable to the body of a user that can measure the heart rate of the user, and is only limited by its ability to measure heart rate of the user.

Figure 2:
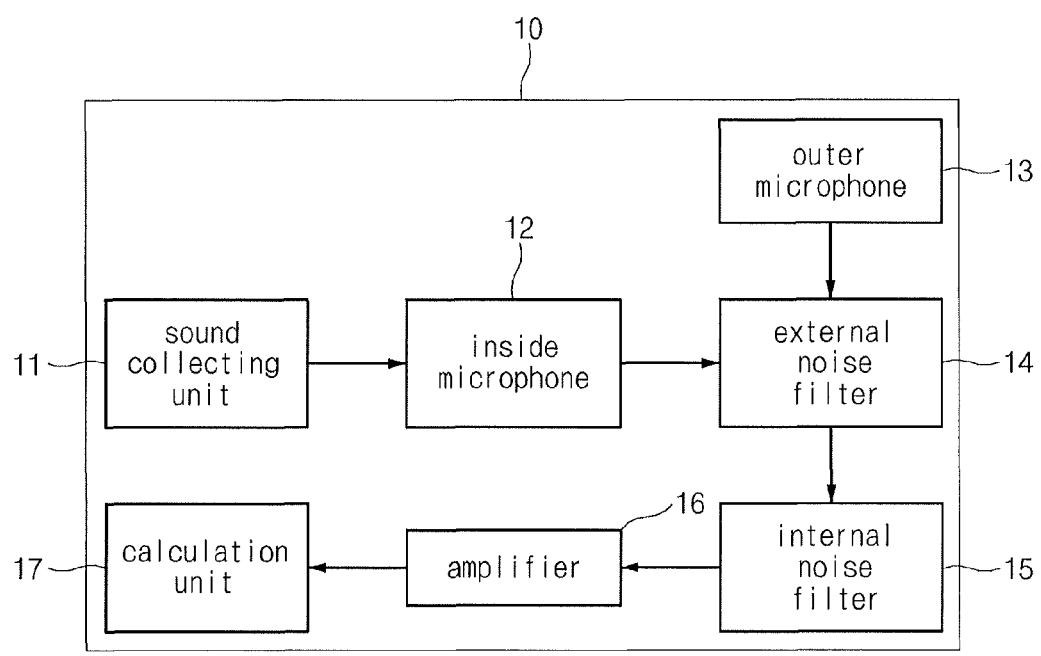
FIG. 2 is a block diagram showing a configuration of an exemplary heart rate measurement system of music selecting system of the present invention.

In another exemplary embodiment of the present invention, for example as shown in FIG. 2, a block diagram shows a configuration of a preferred heart rate measurement system 10 of a music selecting system 100 of the present invention.

For example, as shown in FIG. 2, the heart rate measurement unit 10 preferably includes, but may not only be limited to, a sound collecting unit 11, a inside microphone 12, an outer microphone 13, an external noise filter 14, an internal noise filter 15, an amplifier 16, and a calculation unit 17.

Preferably, the sound collecting unit 11 is suitably installed at the safety belt or a part of the steering wheel which suitably contacts to the breast of the user to collect a sound generated in the breast of the user.

According to preferred related embodiments, the inside microphone 12 suitably converts the sound collected in the sound collecting unit 11 into an electrical signal and sends the converted signal to the external noise filter 14 through a wire or wireless local area network. Here, in the electrically converted sound, a heartbeat sound, an internal noise, and an external noise are suitably mixed.

Preferably, the sound collecting unit 11 and the inside microphone 12 further includes a wireless local area network module (not shown) such as a blue-tooth module, so that it can be comprised of an additional apparatus such as, but not limited to, a wrist watch or a mobile phone. Accordingly, if a user holds the additional apparatus, the sound collecting unit 11 suitably collects a sound which is generated in the breast of the user. The inside microphone 12 preferably converts the collected sound into an electrical signal. Preferably, the wireless local area network module suitably sends the converted signal to the wireless local area network module (not shown) of the external noise filter 14 through a wireless local area network.

According to certain preferred embodiments of the present invention, the outer microphone 13 measures a noise generated in the inside of vehicle, for example, but not limited only to, a vehicle noise, an audio system noise, and a conversation sound. The external noise filter 14 compares the sound which is converted into an electrical signal in the inside microphone 12 with the noise of inside of vehicle which is measured in the outer microphone 13. Preferably, in further embodiments, the external noise filter 14 filters a sound which is similar to the noise of inside of vehicle in the electrically converted signal.

According to further exemplary embodiments, the internal noise filter 15 suitably filters a noise of band which can be considered as a preset band, that is, for example, a noise, in the external noise filter 14. Preferably, the amplifier 16 amplifies the sound filtered in the internal noise filter 15 to suitably amplify the intensity of sound signal.

Figure 3:
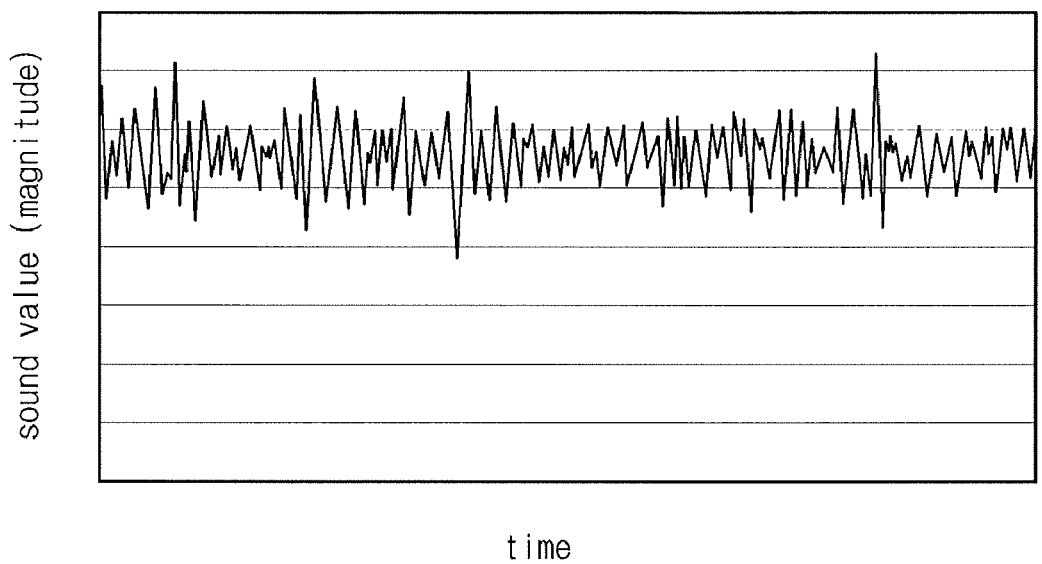
FIGS. 3 to 7 are a graph showing a heart rate calculation process of an exemplary output unit of a music selecting system of the present invention.
Figure 4:
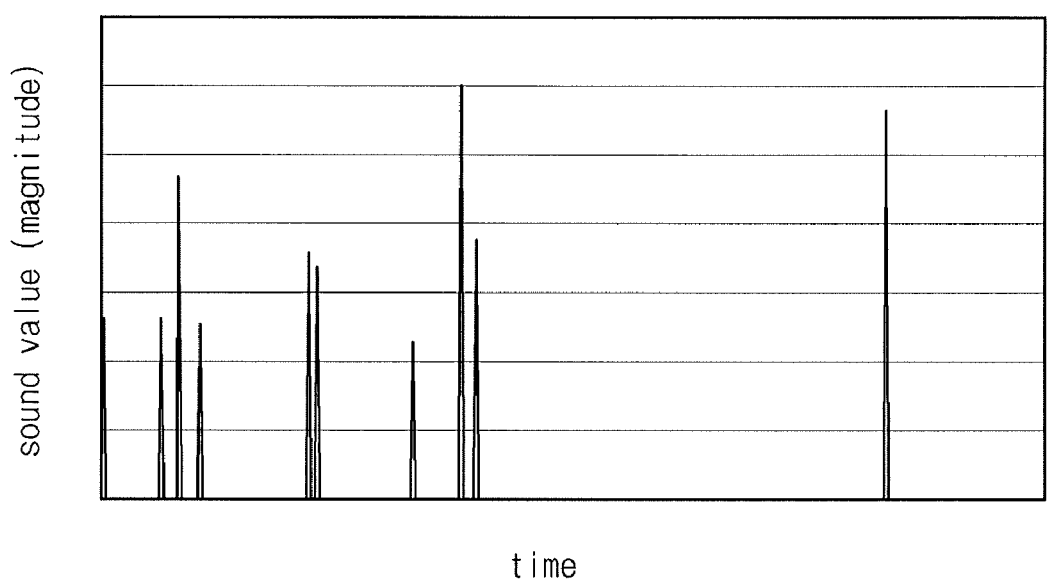

According to further preferred embodiments, the calculation unit 17 preferably indicates the sound as sound values that changes according to a time by oscilloscope (see, for example, FIG. 3). Accordingly, the calculation unit 17 suitably calculates a mean value of the sound values. Preferably, the calculation unit 17 suitably assumes the mean value as 0 and converts all of the sound values of negative value which is suitably smaller than the value 0 into a positive value. Further, the calculation unit 17 squares values which are suitably larger than a mean value among the sound values (see, for example, FIG. 4).

Figure 5:
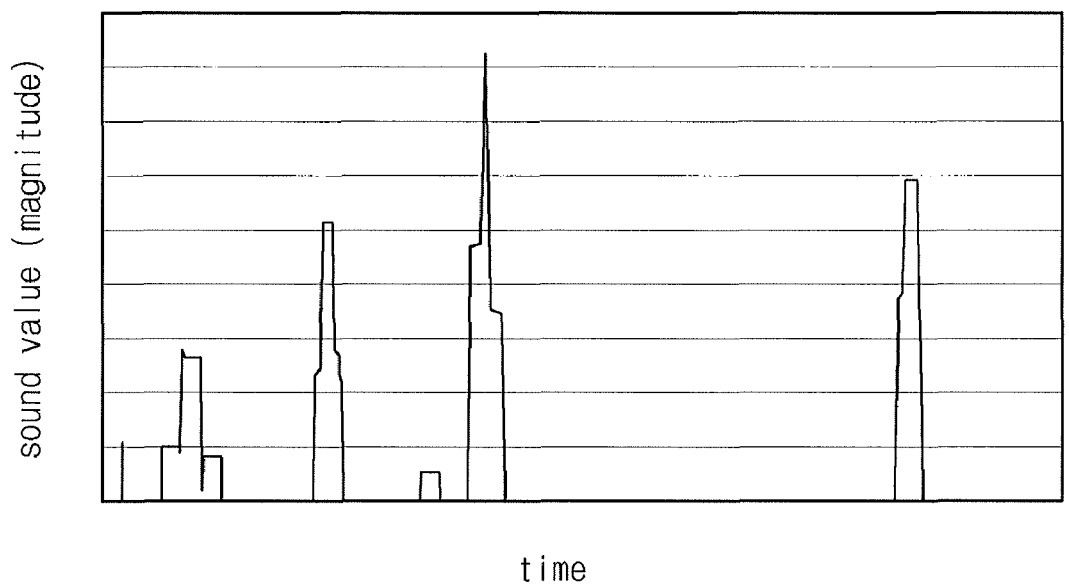
Figure 6:
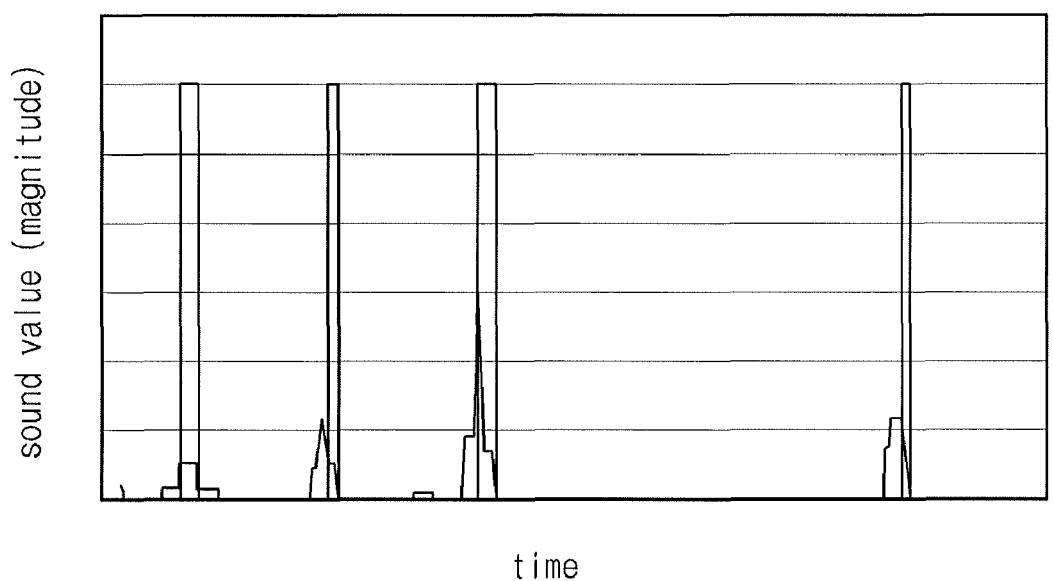

According to further preferred embodiments of the present invention, the sound values which are suitably larger than the mean value are all squared for easy analysis, by preferably comparing with a small sound value to a increased larger sound value. Preferably, the calculation unit 17 indicates the squared sound values as a sound value that changes according to a time by oscilloscope (see, for example, FIG. 5). According to further related embodiments, the calculation unit 17 calculates a mean value of the sound values that changes according to a time and extracts sound values which are suitably higher than a mean value, preferably by as much as a given value (see, for example, FIG. 6). Preferably, the calculation unit 17 suitably calculates a time interval between sound values which are higher than an extracted mean value as much as a given value.

Figure 7:
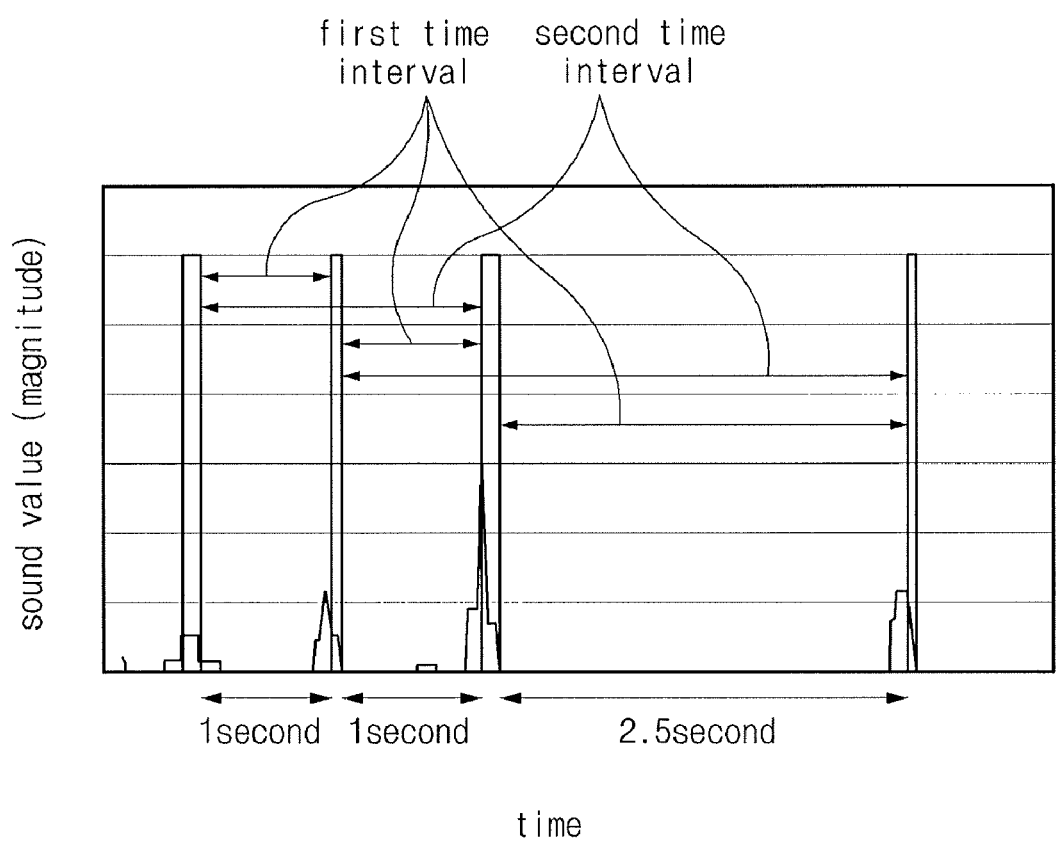

For example, in certain exemplary embodiments and referring for example to FIG. 7, in a preferred state where four sound values which are suitably higher than a mean value by as much as a given value exists, assuming that the four sound values suitably include a first value, a second value, a third value, and a fourth value, a suitable time interval between the first value and the second value, a suitable time interval between the second value and the third value, and a suitable time interval between the third value and the fourth value are preferably called as a first time interval.

In further preferred embodiments, a suitable time interval between the first value and the third value, and a suitable time interval between the second value and the fourth value are preferably called as a second time interval. Preferably, the second time interval is suitably obtained by passing over one sound value, so that, accordingly, it preferably is meant to refer to a suitable time interval between the first value and the third value, and between the second value and the fourth value.

According to certain exemplary embodiments of the present invention, the actual time of time intervals among the obtained first time intervals, for example, the time interval between the first value and the second value of the first time interval becomes 1 second, the time interval between the second value and the third also becomes 1 second, and the time interval between the third value and the fourth value becomes 2.5 seconds.

Preferably, in other exemplary embodiments, the time interval between the first value and the third value of the second time interval becomes 2 seconds and the time interval between the second value and the fourth value becomes about 3.5 seconds. Accordingly, in the time intervals of the first time and the second time, since 1 second was generated total two times and 2 seconds was generated one time and 2.5 seconds was generated one time and 3.5 seconds was generated one time, the time interval of 1 second is preferably most frequently generated among the time intervals. Accordingly, in further related embodiments, by preferably using 1 second which is most frequently generated among the time intervals, the heart rate per a given hour (60 times per 60 second since it is one time in 1 second) is calculated.

According to further preferred embodiments of the present invention, a key input unit 15 is preferably prepared with a keypad and a touch screen, and suitably receives the age (for example, the hour, date and month of birth) from a user. In further embodiments, a biorhythm calculation unit 20 suitably calculates a biorhythm index of the user by using the age of the user which is suitably inputted through the key input unit 15. Preferably, the biorhythm index is suitably made by indexing, for example, the physical, sensitivity, and intellectual of the user.

Figure 8:
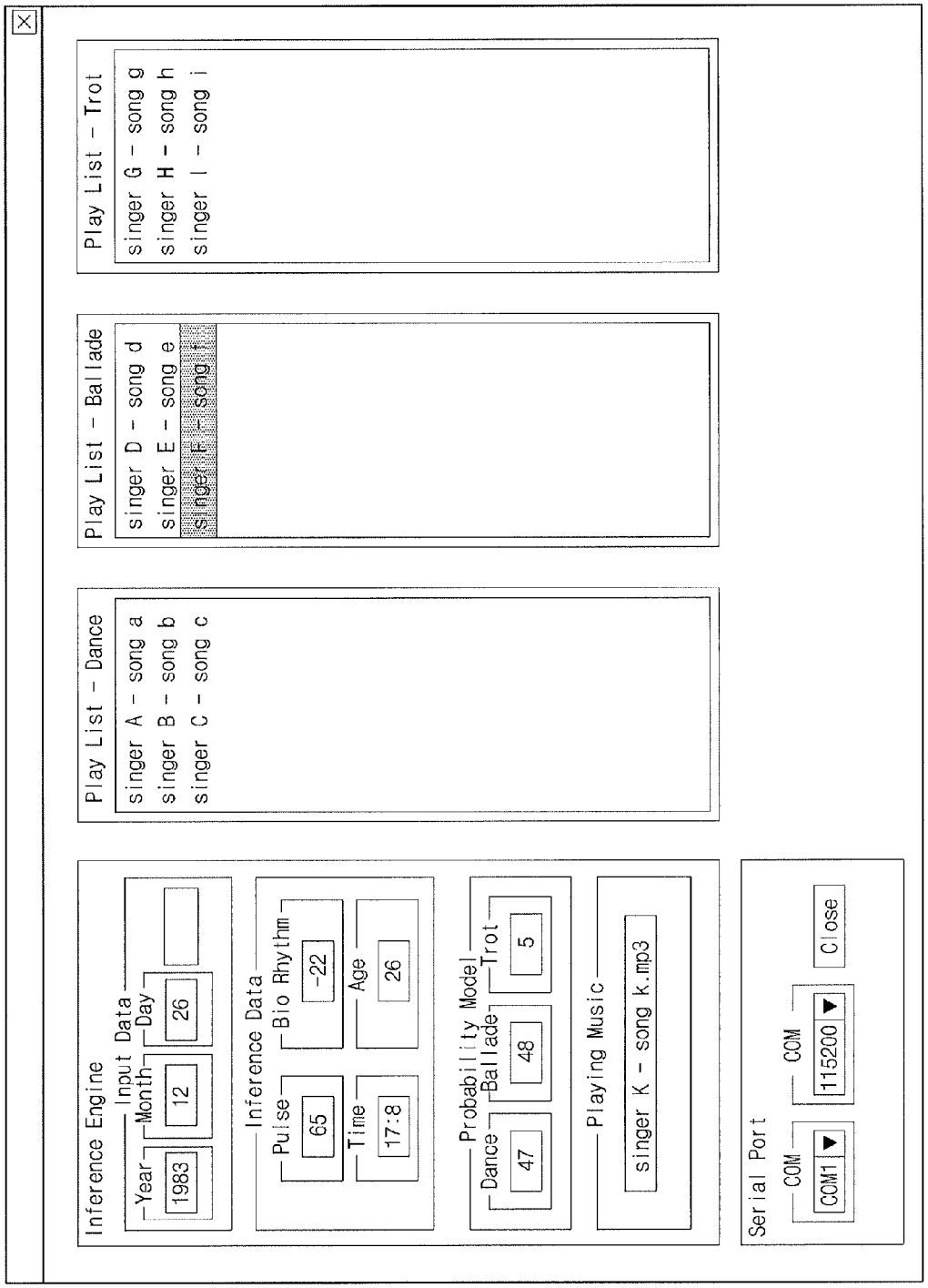
FIG. 8 is a configuration diagram showing a configuration of an exemplary music database of a music selecting system of the present invention.

According to further exemplary embodiments of the present invention, for example as shown in FIG. 8, a configuration diagram shows an exemplary configuration of a music database 50 of a preferred music selecting system 100 of the present invention. For example, and as shown in FIG. 8, the music database 50 suitably stores at least one music file for each of a plurality of genres, for example, but not limited only to, a classical, a dance (or rock, pop or the like), and a ballad genre.

According to other exemplary embodiments of the present invention, for example as shown in FIG. 9, a configuration diagram shows a configuration of emotional quotient database 30 of music selecting system 100 of the present invention.

As shown in FIG. 1, the emotional quotient database 30 suitably stores emotional quotients according to a biorhythm index by heartbeat quotient preferably according to the key input unit 15 or by a difference between an average heart rate of the user which is previously measured and a current heart rate of the user.

For example, in certain exemplary embodiments, when the average heart rate of the user is 60 times and the current heart rate is measured as 71 times, which exceeds the average heart rate of the user by 10 times, it is suitably classified as "fast". In related embodiments, when the current heart rate is suitably measured in the interval of −10 to +10 times of 60 times, that is, if it is suitably measured in the range of 50 to 70 times, it is preferably classified as "middle". In further embodiments, when the current heart rate is suitably measured to be below the 10 times from the 60 times, that is, if it is suitably measured to be 49 times and less, it is preferably classified as "slow".

In the preferred biorhythm index, 34~100 is suitably classified as "high" and −34 to +34 is suitably classified as "middle", and −100 to −33 is suitably classified as "low". Accordingly, in certain preferred embodiments of the invention, in the emotional quotient database 30, the emotional quotients according to the biorhythm index by heartbeat quotient are preferably quantified with a score of 30 (heart rate: slow, biorhythm index: low) to 70 (heart rate: fast, biorhythm index: high).

According to further exemplary embodiments of the present invention, for example as shown in FIG. 10, a configuration diagram shows a configuration of time quotient database 40 of music selecting system 100 of the present invention.

As shown in FIG. 10, the time quotient database 40 suitably stores a time quotient by time. For example, it can be set as 0 point in the early morning (00:00 to 06:00), +20 point in the office-going hour (06:01 to 09:00), −10 point in the forenoon (09:01 to 12:00), +10 point in the lunchtime (12:01 to 14:00), 0 point in the afternoon (14:01 to 18:00), and −10 point in the evening (18:01 to 24:00).

Figure 11:
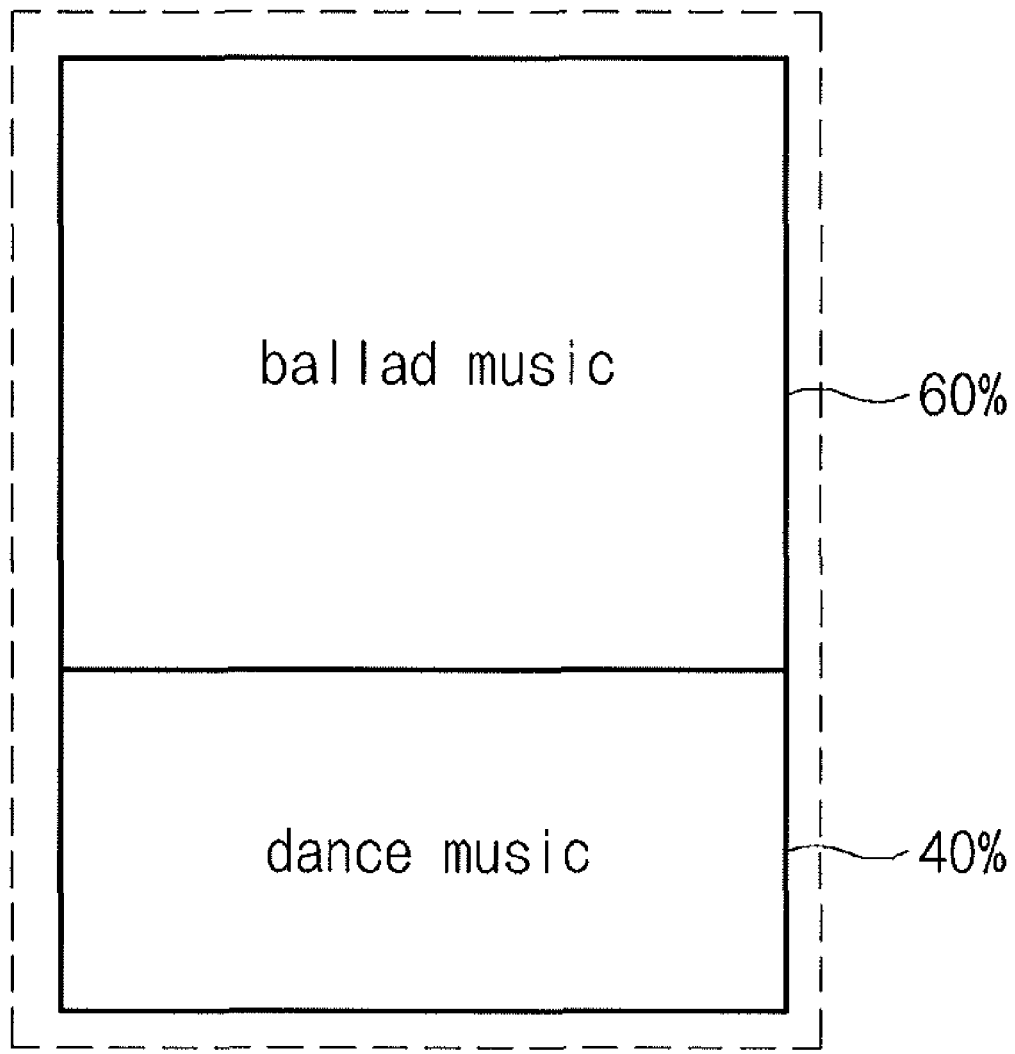
FIG. 11 is a configuration diagram showing an emotional quotient and genre combination quotient by time of an exemplary music selecting system of the present invention.
Figure 12B:
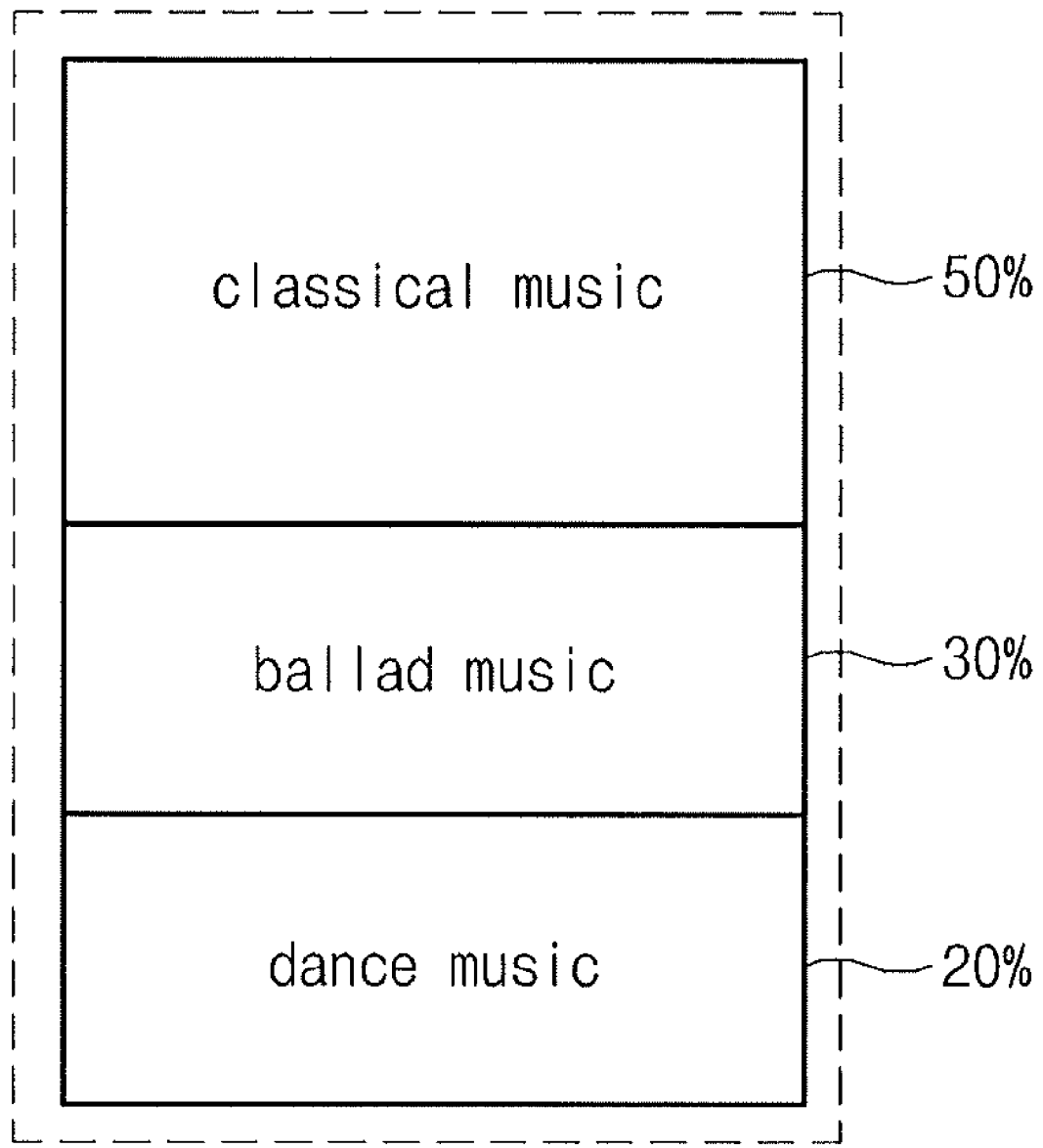

According to further exemplary embodiments of the present invention, for example as shown in FIG. 11, a configuration diagram shows a genre combination quotient by emotional quotient and time of music selecting system 100 of the present invention, and FIGS. 12a and 12b show a configuration of genre combination quotient by age of music selecting system 100 of the present invention.

Preferably, the genre combination quotient database 60 suitably stores the genre combination quotient by emotional quotient and time and the genre combination quotient by age. For example, the genre combination quotient according to emotional quotient and time quotient is an quotient which suitably indicates which genre will be more reflected among two specific genres, for example, the ballad and the dance, according to the summation quotient of the emotional quotient and the time quotient.

For example, when the summation quotient is 60 point, the music genre reflection rate becomes dance music (60): ballad music (40). Accordingly, referring, for example, to FIG. 11, the dance music genre can be suitably selected with the rate of 60%, while the ballad music genre can be selected with the rate of 40% (for example, when 10 songs are selected, 6 dance songs and 4 ballad songs are selected).

According to further exemplary embodiments of the present invention, for example as shown in FIG. 12, the genre combination quotient by age suitably indicates which specific genre, for example, the classical music genre, will be preferentially reflected to the music genre reflection rate. For example, in certain preferred embodiments, the rate of 5% for one's twenties, 30% for one's thirties, 40% for one's forties, 50% for one's fifties, 55% for one's sixties, and 60% for one's seventies are stored. According to further exemplary embodiments, such a genre combination quotient by age is suitably made based on the result of searching a favorite music genre by age. In other certain embodiments, as an example, if one's twenties does not like the classical music genre, only 5% is firstly reflected to the classical music, whereas 60% is firstly reflected to the classical music genre for one's seventies, as classical music genre is preferred.

Accordingly, as shown in FIG. 12b, in the music genre reflection rate according to the genre combination quotient by emotional quotient and time, if the genre combination quotient by age is suitably reflected into the rate of dance music (60): ballad music (40), in case of one's fifties, the classical music is firstly reflected with the reflection rate 50%, so that the music genre reflection rate preferably becomes classical music (50): dance music (30): ballad music (20).

According to further preferred embodiments of the present invention, the controller 70 calculates the emotional quotient by using the heart rate and biorhythm index of the user. Further, the controller 70 suitably calculates the music genre reflection rate in consideration of the emotional quotient, and the current time quotient. For example, if the summation point of the emotional quotient and the current time quotient is 60 point, the dance genre is suitably assigned with the rate of 60% while the rest 40% is assigned to the ballad.

In other exemplary embodiments, if the age of the user is one's fifties, the controller 70 suitably assigns the rate of 50% to the classical music based on the rate of 50% of the genre combination quotient by age, and then, reflects the rate of 50% into the rate of dance music (60): ballad music (40), so that the final music genre reflection rate is suitably determined to be classical music (50): dance music (30): ballad music (20).

Accordingly, the controller 70 suitably selects the specific music genre according to the calculated music genre reflection rate. For example, when randomly performing a music selection for 10 songs, the controller 70 selects 5 classical music, 3 dance music, and 2 ballad music according to the rate of classical music (50): dance music (30): ballad music (20). In preferred exemplary embodiments, the playing unit 80 plays a music file suitably selected by the controller 70 through the speaker 90. Preferably, the speaker 90 outputs the music file played in the playing unit 80.

Preferably, the user satisfaction level confirmation unit 95 receives the satisfaction level of the music file selected through the key input unit 15 and suitably sends it to the controller 70. Accordingly, the controller 70 suitably modifies the genre combination quotient stored in the genre combination quotient database 60. Hereinafter, the operation of music selecting system 100 of the present invention is illustrated.

Figure 13:
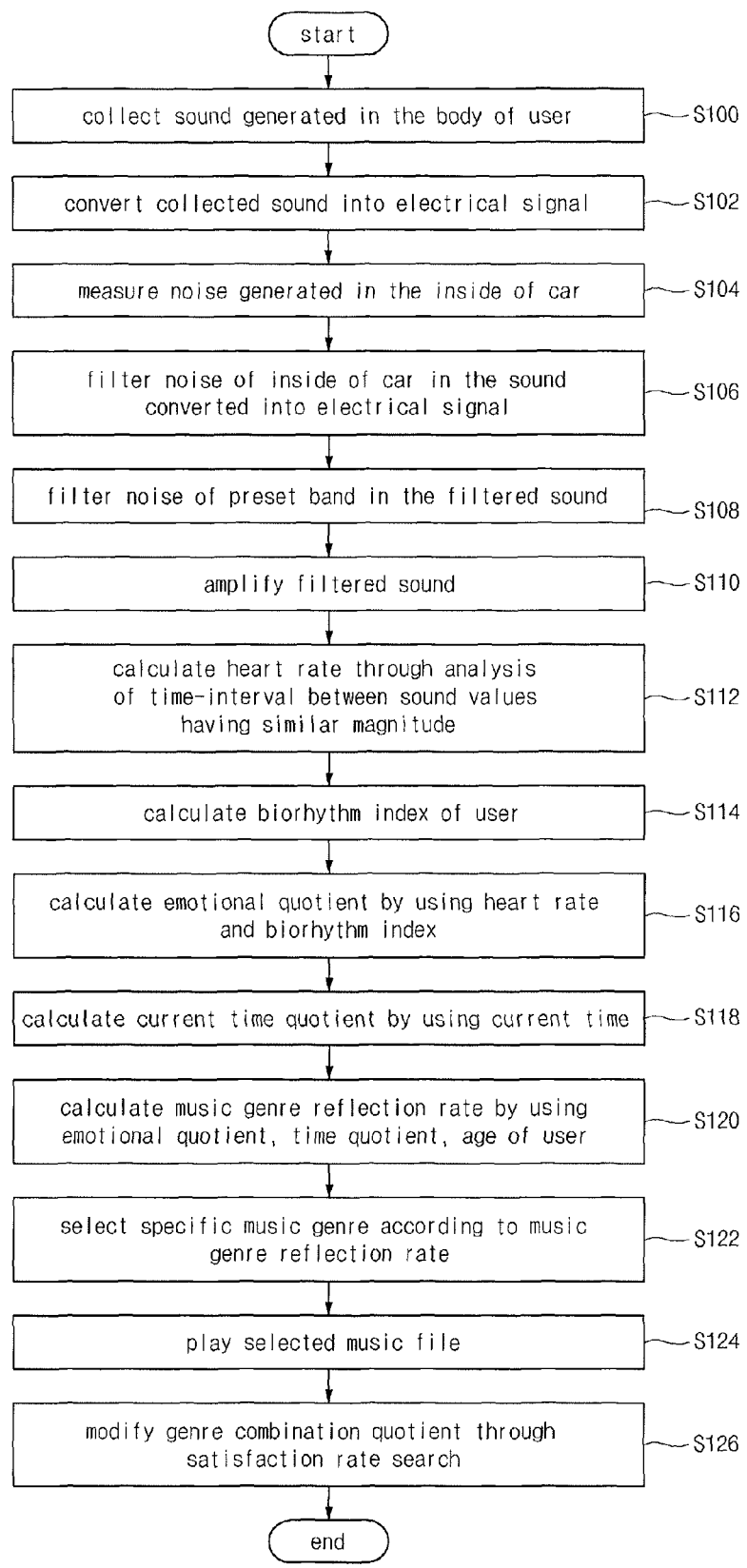
FIG. 13 is a flowchart showing preferred exemplary operation of music selecting system of the present invention.

According to further exemplary embodiments of the present invention, for example as shown in FIG. 13, a flowchart shows an operation of music selecting system 100 of the present invention.

According to further exemplary embodiments of the present invention, for example as shown in FIG. 13, when a user gets on vehicle and preferably fastens a seat belt, the sound collecting unit 11 of the heart rate measurement unit 10 is suitably contacted with a breast part of the user and collects a sound generated in the body of the user (S100). Preferably, the inside microphone 12 of the heart rate measurement unit 10 then suitably converts the collected sound into an electrical signal (S102).

According to further embodiments, the outer microphone 13 of the heart rate measurement unit 10 suitably measures a noise generated in the inside of vehicle (S104). Preferably, the outer microphone 13 of the heart rate measurement unit 10 filters a sound which is similar to the noise of the inside of vehicle measured in the outer microphone 13 in the sound converted into an electrical signal in the inside microphone 12 (S106). Further, the internal noise filter 15 of the heart rate measurement unit 10 suitably filters a noise of preset band in a sound filtered in the external noise filter 14 (S108). Preferably, the amplifier 16 of the heart rate measurement unit 10 suitably amplifies the sound filtered in the internal noise filter 15 (S110).

Preferably, the calculation unit 17 of the heart rate measurement unit 10 suitably calculates the heart rate of the user through an analysis of time-interval between sound values having a similar magnitude in the measured sound value (S112). In related embodiments, the biorhythm calculation unit 20 suitably calculates the biorhythm index of the user, preferably by using the age of the user suitably received through the key input unit 15 (S114).

Then, in further related embodiments, the controller 70 suitably calculates the emotional quotient by using the emotional quotient database 30, the heart rate and biorhythm index of the user (S116). Preferably, the controller 70 calculates the current time quotient by using the time quotient database 40 and the current time received from an additional timer (S118). The controller 70 preferably calculates the music genre reflection rate according to a user with reference to the emotional quotient, the time quotient, the age of the user and the genre combination quotient database 60 (S120).

In further embodiments, the controller 70 then preferably selects the specific music genre according to the calculated music genre reflection rate, and preferably selects a music file according to the selected music genre from the music file database (S122). Then, according to further preferred embodiments, the playing unit 80 plays the selected music file through the speaker 90 (S124). Preferably, the satisfaction level confirmation unit suitably receives the satisfaction level of the selected music file through the key input unit 15 and suitably sends it to the controller 70.

Preferably, the controller 70 suitably modifies the genre combination quotient stored in the genre combination quotient database through the satisfaction level of the sent music file (S126). Accordingly, in further preferred embodiments, the controller 70 can control the genre reflection rate of dance, classical, and ballad according to the emotional quotient, the current time quotient and the age, in the genre combination quotient through the satisfaction level of the music file. An preferred exemplary embodiment of the present invention is described herein below.

According to further exemplary embodiments of the present invention, for example as shown in FIGS. 11, 12*a*, 12*b*, it is assumed that the average heart rate of the user is 60 times per minute and the heart rate measured by the heart rate measurement unit 10 is 70 times and the current biorhythm index of the user is 55 and the current time is a lunch time (for example, 12:00 eastern standard time) and the age of the user is one's fifties.

Accordingly, a difference between the average heart rate and the current heart rate becomes +10 and the biorhythm index is 55, so that the emotional quotient becomes 70. Preferably, the current time quotient becomes +10 since it is a lunch time. Accordingly, the genre combination quotient by emotional quotient and time becomes 80 as it is 70+10, so that it is preferably set with the rate of ballad music (20): dance music (80). Accordingly, in preferred exemplary embodiments, the genre combination quotient by age becomes 50% as the age of the user is one's fifties, so that, in the music genre reflection rate, 50% is firstly reflected for the classical music to the rate of ballad music (20): dance music (80).

Accordingly, the finally calculated music genre reflection rate preferably becomes classical music (50): ballad music (10): dance music (40), so that, in case of selecting 10 songs, 5 classical music, 1 ballad music, and 4 dance music are selected. Preferably, for example, if the emotional quotient is 80 point which is a high point, it corresponds to a suitably rapid pulse and the biorhythm is suitably high, so that it is a state where the probability of stimulating a mood and reaching a climax is suitably increased. Accordingly, the dance music is assigned with 80% while the ballad music is assigned with 20%. In certain exemplary embodiments, if an individual in one's fifties may prefer the classical music genre, 50% among them is firstly assigned for the classical music.

In further related embodiments, if the emotional quotient is 20 point which is a suitably low point, it corresponds to a suitably slow pulse, and accordingly corresponds to a state of being suitably calm and inactive. Accordingly, the ballad music is preferably assigned with 80% while the dance music is assigned with 20%.

Accordingly, if a user is one's twenties, the probability of selecting the classical music is suitably lowered, so that the classical music is preferably reflected with 5%. Accordingly, the music genre reflection rate becomes classical (5): ballad (76): dance (19). Thus, in case of selecting 100 songs, 5 classical songs, 76 ballad songs, and 19 dance songs can be selected.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A music selecting system, comprising:
a heart rate measurement unit that measures a heart rate of a user;
a biorhythm calculation unit that calculates a biorhythm index of the user;
a music database that stores at least one music file for each of a plurality genres; and
a controller configured to calculate an emotional quotient that corresponds to the heart rate and the biorhythm index of the user based on emotional quotients stored in an emotional quotient database and calculated based on a range of heart rates and the biorhythm index, and selects a music file of a specific music genre for the user in consideration of a genre combination quotient according to the emotional quotient, a current time quotient and an age.

2. The music selecting system of claim 1, wherein the controller calculates a music genre reflection rate according to the user by using the genre combination quotient and selects the music file according to the calculated music genre reflection rate.

3. The music selecting system of claim 1, further comprising:
an emotional quotient database that stores emotional quotients according to a biorhythm index by heartbeat quotient according to a difference between an average heart rate of the user which is previously registered and a current heart rate of the user;
a time quotient database that stores a time quotient by time; and
a genre combination quotient database that stores a genre combination quotient by emotional quotient and time and a genre combination quotient by age.

4. The music selecting system of claim 1, wherein the heart rate measurement unit comprises:
a sound collecting unit that collects a sound generated in a body of the user;
an inside microphone that converts the collected sound into an electrical signal;
an outer microphone that measures a noise generated in the inside of a vehicle;
an external noise filter that filters a sound which is similar to the measured sound from the converted sound;
an internal noise filter that filters a noise of preset band from the sound filtered in the external noise filter;
an amplifier that amplifies the sound filtered in the internal noise filter; and
a calculation unit that analyzes time intervals between values of the amplified sound and calculates a heart rate per hour by using a time interval which most frequently happens among the time intervals.

5. The music selecting system of claim 4, wherein the sound collecting unit and the inside microphone are comprised of an independent device including a wireless communications module to send the sound which is converted into an electrical signal through the wireless communications module to the external noise filter.

6. The music selecting system of claim 4, wherein the calculation unit squares all values which are larger or smaller than a mean value among the sound values, extracts sound values which are higher than a given value among the squared sound values and calculates time intervals between the extracted sound values, and calculates a heart rate per hour by using a time interval which most frequently happens among the time intervals.

7. The music selecting system of claim 1, wherein the music database stores at least one music file for each of music genres including a classical music, a ballad music and a dance music.

8. The music selecting system of claim 1, further comprising:
a playing unit that plays a music file selected by the controller through a speaker; and
a key input unit that receives an age from a user.

9. The music selecting system of claim 1, further comprising a user satisfaction level confirmation unit that receives a satisfaction level of music file selected through the key input unit and sends it to the controller, and modifies a genre combination quotient stored in a genre combination quotient database through the satisfaction level of the sent music file.

10. A music selecting method, comprising:
(a) measuring a heart rate of a user;
(b) calculating a biorhythm index of the user; and
(c) calculating an emotional quotient that corresponds to the heart rate and the biorhythm index of the user based on emotional quotients stored in an emotional quotient database and calculated based on a range of heart rates and the biorhythm index, and selecting a music file of a specific music genre for the user in consideration of a genre combination quotient according to the emotional quotient, a current time quotient and an age.

11. The music selecting method of claim 10, wherein, in the step of (c), a music genre reflection rate according to user is calculated by using the genre combination quotient and the music files are selected according to the calculated music genre reflection rate.

12. The music selecting method of claim 10, wherein the step of (a) comprises:
(a-1) collecting a sound generated in a body of the user;
(a-2) converting the collected sound into an electrical signal;
(a-3) measuring a noise generated in the inside of vehicle;
(a-4) filtering a sound which is similar to a noise of the inside of vehicle measured in an outer microphone in a sound which is converted into an electrical signal in an inside microphone;
(a-5) filtering a noise of preset band in an external noise filter;
(a-6) amplifying a sound filtered in an internal noise filter; and
(a-7) calculating a heart rate per hour by using a time interval which most frequently happens among the time intervals by analyzing time intervals between values of the amplified sound.

13. The music selecting method of claim 12, wherein the step of (a-7) squares all values which are larger or smaller than a mean value among the amplified sound values, extracts sound values which are higher than a given value among the squared sound values and calculates time intervals between the extracted sound values, and calculates a heart rate per hour by using a time interval which most frequently happens among the time intervals.

14. A music selecting system, comprising:
a heart rate measurement unit that measures the heart rate of a user;
a biorhythm calculation unit that calculates a biorhythm index of the user;
a music database that stores at least one music file;
a controller that selects a music file, wherein the controller calculates an emotional quotient the heart rate and the biorhythm index of the user based on emotional quotients stored in an emotional quotient database and calculated based on a range of heart rates and the biorhythm index.

15. The music selecting system of claim 14, wherein the music database stores at least one music file for one or more music genres.

16. The music selecting system of claim 14, wherein the controller further selects a music file of a specific music genre for the user in consideration of a genre combination quotient according to the emotional quotient, a current time quotient and an age.

17. A motor vehicle comprising the music selecting system of claim 1.

18. A motor vehicle comprising the music selecting system of claim 14.

19. A music selecting method, comprising:
(a) measuring a heart rate of a user;
(b) calculating a biorhythm index of the user; (c) calculating an emotional quotient by using the heart rate and biorhythm index of the user based on emotional quotients stored in an emotional quotient database and calculated based on a range of heart rates and the biorhythm index, and selecting a music file for the user; and the music file is of a specific music genre.

20. The method of claim 19, wherein the selection of a music file for the user is in consideration of a genre combination quotient according to the emotional quotient, a current time quotient and an age.

\* \* \* \* \*